US012611252B2

(12) United States Patent
Vandebroek et al.

(10) Patent No.: US 12,611,252 B2
(45) Date of Patent: Apr. 28, 2026

(54) ADD-ON DEVICE FOR SURGICAL INSTRUMENT

(71) Applicant: Katholieke Universiteit Leuven, Leuven (BE)

(72) Inventors: Tom Vandebroek, Leuven (BE); Emmanuel Vander Poorten, Mechelen (BE)

(73) Assignee: Katholieke Universiteit Leuven, Leuven (BE)

( * ) Notice: Subject to any disclaimer, the term of this patent is extended or adjusted under 35 U.S.C. 154(b) by 397 days.

(21) Appl. No.: 18/485,694

(22) Filed: Oct. 12, 2023

(65) Prior Publication Data

US 2024/0122647 A1 Apr. 18, 2024

Related U.S. Application Data

(60) Provisional application No. 63/379,258, filed on Oct. 12, 2022.

(51) Int. Cl.
*A61B 18/22* (2006.01)
*A61B 18/14* (2006.01)
*A61B 18/00* (2006.01)

(52) U.S. Cl.
CPC .......... *A61B 18/22* (2013.01); *A61B 18/1492* (2013.01); *A61B 2018/00172* (2013.01); *A61B 2018/00595* (2013.01); *A61B 2018/00601* (2013.01)

(58) Field of Classification Search
CPC ..................... A61B 2018/00172; A61B 18/22
See application file for complete search history.

(56) References Cited

U.S. PATENT DOCUMENTS

| | | | | |
|---|---|---|---|---|
| 5,766,164 A * | 6/1998 | Mueller | ................. | A61B 18/22 606/17 |
| 5,861,002 A * | 1/1999 | Desai | .................... | A61M 1/774 606/139 |
| 6,152,918 A * | 11/2000 | Padilla | ................... | A61B 18/22 606/7 |
| 7,226,444 B1 * | 6/2007 | Ellman | ................. | A61B 18/22 606/41 |

* cited by examiner

*Primary Examiner* — Sung H Pak
(74) *Attorney, Agent, or Firm* — TraskBritt

(57) ABSTRACT

A device for removably coupling a laser fiber to a shaft of a surgical instrument is disclosed. The device comprises at least a first and a second coupling element for coupling the fiber to the instrument, each of the coupling elements comprising a respective first aperture for slidably coupling to a laser fiber and a respective second aperture for fixedly coupling to the instrument; the first and second coupling elements being spaced apart in a second direction parallel to the first direction, the first element being positioned such that when coupled to the instrument, the first element is located between a first end of the shaft and the second element, the first and second element being spaced apart in the second direction by a separation that is greater than or equal to the product of the minimal bending radius and the maximum expected bending angle of the fiber; the device further comprises an actuation element connected between two coupling elements, the actuation element comprising a connector for fixedly coupling to the fiber; wherein the actuation element is configured to translate the connector along the second direction when actuated.

20 Claims, 9 Drawing Sheets

ADD-ON DEVICE FOR SURGICAL INSTRUMENT

CROSS-REFERENCE TO RELATED APPLICATION

This application claims the benefit under 35 U.S.C. § 119(e) of U.S. Provisional Patent Application Ser. No. 63/379,258, filed Oct. 12, 2022, the disclosure of which is hereby incorporated herein in its entirety by this reference.

TECHNICAL FIELD

This application relates to an add-on device for coupling a laser fiber to a surgical instrument.

BACKGROUND

Introduced in 2006, transoral robotic surgery (TORS) is established as a treatment option with good oncological and functional outcomes for selected malignancies in the upper aerodigestive tract. A commonly used robotic system, Da Vinci (Intuitive Surgical Inc., Sunnyvale, CA, USA), provides the surgeon with a three-dimensional view of the operating field and with considerable dexterity, thanks to the combination of endo-wristed instruments with seven degrees of freedom (DOF) and the elimination of physiological tremor. In this way, TORS enables the surgeon to adhere to the oncological principle of en-bloc tumor resection, avoiding piecemeal resection, thus facilitating histopathological assessment of the tumor and surgical margins. This is in contrast to the piecemeal resection that results from the longer existing and competing technique of transoral laser microsurgery (TLM). During TLM, tumors are removed through a narrow laryngo- or oropharyngoscope under a microscopic view by a micromanipulator-controlled $CO_2$-laser fixed to the microscope, resulting in a tangential-only cutting plane ("line of sight" issue). On the other hand, electrocautery is incorporated in the da Vinci system as a monopolar spatula or monopolar scissors, mounted on one of the robotic arms, and is a commonly used surgical cutting and hemostatic tool for TORS.

When compared to a $CO_2$-laser, monopolar cautery causes significantly more collateral tissue damage as well as specimen coagulation, which can complicate margin assessment. Another issue is that coagulated tissue can end up sticking to the spatula tip. This then frequently needs to be removed intra-operatively, in order to be able to perform fine dissection. Flexible hollow wave guides can be used to add $CO_2$ laser functionality to the robotic setup. Advantages of use of a $CO_2$ laser over electrocautery are (1) a more precise cutting, (2) effective hemostasis of vessels of 0.5 mm or less, (3) lymphatic sealing by laser, preventing tumor spread, and (4) a reduced thermal injury resulting in less postoperative edema. However (2) has also as disadvantage that any vessel larger than 0.5 mm cannot be coagulated by the laser; while the monopolar spatula can.

"Transoral Robot-Assisted $CO_2$ Laser Supraglottic Laryngectomy: Experimental and Clinical Data," Solares et al., *The Laryngoscope* 117(5):817-20, January 2009, describes use of a hollow core fiber allowing the transmission of $CO_2$ laser energy linked to a daVinci Surgical Robot. A sheath was used to attach the laser fiber to a robotic arm. Translation of the laser fiber relative to the arm was thus not possible.

The FibreLase™ Robotic Drop-In Guide (Lumenis Ltd., Israel) is a drop-in guide that can be grabbed by a robotic needle driver. The drop-in guide requires use of the entire functionality of the needle-driver needed to position it, meaning that the drop-in guide cannot be combined with another instrument such as a monopolar spatula while occupying its robotic arm. Thus the entire robotic arm is occupied by the drop-in-guide alone. Consequently, when the surgeon is confronted with bleeding from vessels with a diameter of more than 0.5 mm during $CO_2$-laser TORS, hemostasis relies on the assistant surgeon sitting at the head of the table. The assistant then needs to introduce an additional instrument and by means of, e.g., a suction/cautery device or hemostatic clips try to stop the bleeding. This can be especially difficult when bleeding arises deep in the aerodigestive tract (e.g., hypopharyngeal location) due to space constraints. An alternative, but time consuming option is to interrupt the surgery and switch the needle driver for a monopolar spatula. Moreover, the drop-in guide—needle driver combination is not suitable for blunt dissection, which is an essential feature of the monopolar spatula during TORS. Recently, a number of alternative systems for minimally invasive robotic surgery have been introduced such as the Senhance system from Transenterix, the REVO-I system from Meere Company, the Avatera from Avateramedical, the MIRO from Medtronic, the Versius from Cambridge Robotics or the Hugo RAS system from Medtronic.

BRIEF SUMMARY

According to a first aspect of the disclosure, there is provided a device for removably coupling a laser fiber to a shaft of a surgical instrument, the shaft extending in a first direction, the device comprising at least a first and a second coupling element for coupling the fiber to the instrument, each of the coupling elements comprising a respective first aperture for slidably coupling to a laser fiber and a respective second aperture for fixedly coupling to the instrument; the first and second coupling elements being spaced apart in a second direction parallel to the first direction, the first element being positioned such that when coupled to the instrument, the first element is located between a first end of the shaft and the second element, the first and second element being spaced apart in the second direction by a separation that is greater than or equal to the product of the minimal bending radius and the maximum expected bending angle of the fiber; the device further comprising an actuation element connected between two coupling elements, the actuation element comprising a connector for fixedly coupling to the fiber; wherein the actuation element is configured to translate the connector along the second direction when actuated.

It has been found that by providing an actuation element coupled to the fiber that can move relative to the coupling elements, the fiber can be easily translated relative to the instrument. It is an advantage of embodiments of the disclosure that, by providing more than one point of connection to the fiber, the fiber can be bent in a controllable manner.

In situations where an instrument and fiber need to access a confined space through a small incision (e.g., minimally invasive surgery), it is important that the curvature of the instrument and fiber are minimal and the fiber Instrument system can be introduced straight through that incision. Embodiments of the disclosure provide this functionality since the at least two coupling elements and the actuation element can be aligned in the same direction.

The actuation element may comprise at least one artificial muscle. An artificial muscle advantageously provides controllable displacement of the actuation element relative to the coupling elements.

The actuation element may comprise at least one spring. The connector may connect the spring and the artificial muscle. The combination of a spring and a muscle provides a simple linear actuation system that can return to a neutral state due to the biasing behavior of the spring.

The actuation element may comprise a cable and the device comprises a motor for actuating the cable.

The maximum expected bending angle may be between 10 and 90 degrees.

The device may comprise a third coupling element, wherein the second coupling element is located between the first and the third coupling elements in the second direction, wherein the actuation element is connected between the second and the third coupling element. By providing a third coupling element with the actuation mechanism located between the second and third coupling elements, the actuation mechanism can be located outside the patient cavity so that the diameter needed inside the workspace is not increased by the need to accommodate the actuation mechanism.

Embodiments comprising only two coupling elements are advantageously smaller and mechanically simpler, thus being easier to repair/replace.

The device may comprise a rigid sheath that extends over the second and third elements and the actuation element. The sheath advantageously protects the actuation mechanism from damage during operation. The sheath also advantageously solidarizes the second and the third elements so that the actuation mechanism can be slid onto the instrument as one rigid body, making assembly easier and faster.

The device may comprise comprising a bendable sheath that extends between the first and second elements for enclosing a portion of the laser fiber between the first and second elements. The sheath advantageously protects the fiber and the actuation mechanism from damage during operation when the actuation mechanism is located between the first and second coupling elements.

According to a second aspect of the disclosure, there is provided a system comprising a device according to the first aspect and a control module comprising control means for controlling a position of the connector relative to the coupling elements and means for estimating the motion of the actuator, for measuring the configuration of the device or for measuring the displacement of the laser fiber.

DETAILED DESCRIPTION

Figure 1A:
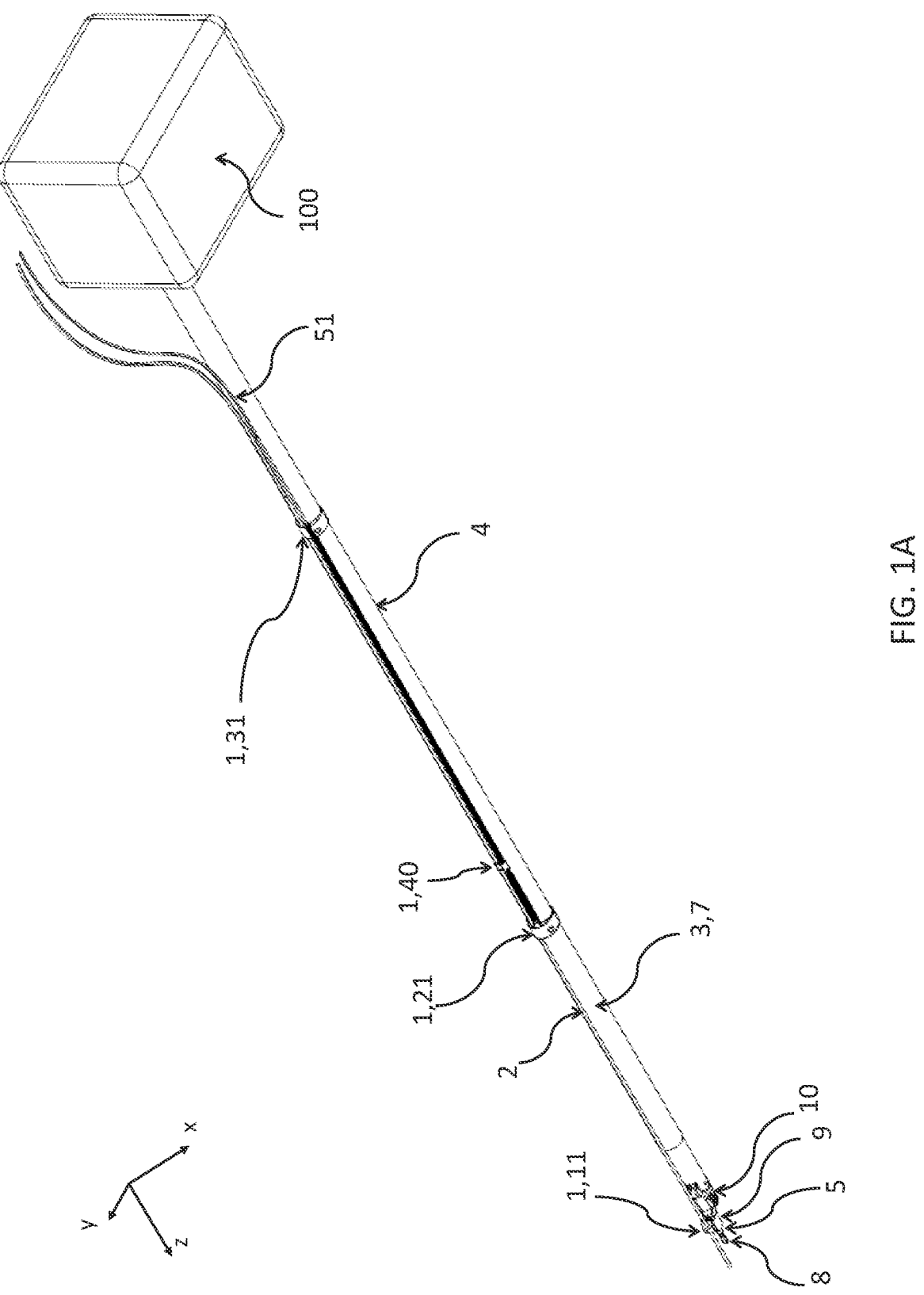
FIG. 1A is a perspective view of a device according to embodiments of the disclosure when coupled to a laser fiber and a surgical instrument.

The disclosure will be described with respect to particular embodiments and with reference to certain drawings but the disclosure is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the disclosure.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the disclosure described herein are capable of operation in other sequences than described or illustrated herein.

Moreover, the terms before, after, and the like in the description and the claims are used for descriptive purposes and not necessarily for describing relative positions. It is to be understood that the terms so used are interchangeable with their antonyms under appropriate circumstances and that the embodiments of the disclosure described herein are capable of operation in other orientations than described or illustrated herein.

It is to be noticed that the term "comprising," used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. The term "comprising," therefore, covers the situation where only the stated features are present and the situation where these features and one or more other features are present. Thus, the scope of the expression "a device comprising means A and B" should not be interpreted as being limited to devices consisting only of components A and B. It means that with respect to the disclosure, the only relevant components of the device are A and B.

Reference throughout this specification to "one embodiment" or "an embodiment" means that a particular feature, structure or characteristic described in connection with the embodiment is included in at least one embodiment of the disclosure. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the disclosure, various features of the disclosure are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed disclosure requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this disclosure.

Furthermore, while some embodiments described herein include some but not other features included in other embodiments, combinations of features of different embodiments are meant to be within the scope of the disclosure, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the disclosure.

In the description provided herein, numerous specific details are set forth. However, it is understood that embodiments of the disclosure may be practiced without these specific details. In other instances, well-known methods, structures and techniques have not been shown in detail in order not to obscure an understanding of this description.

Figure 1B:
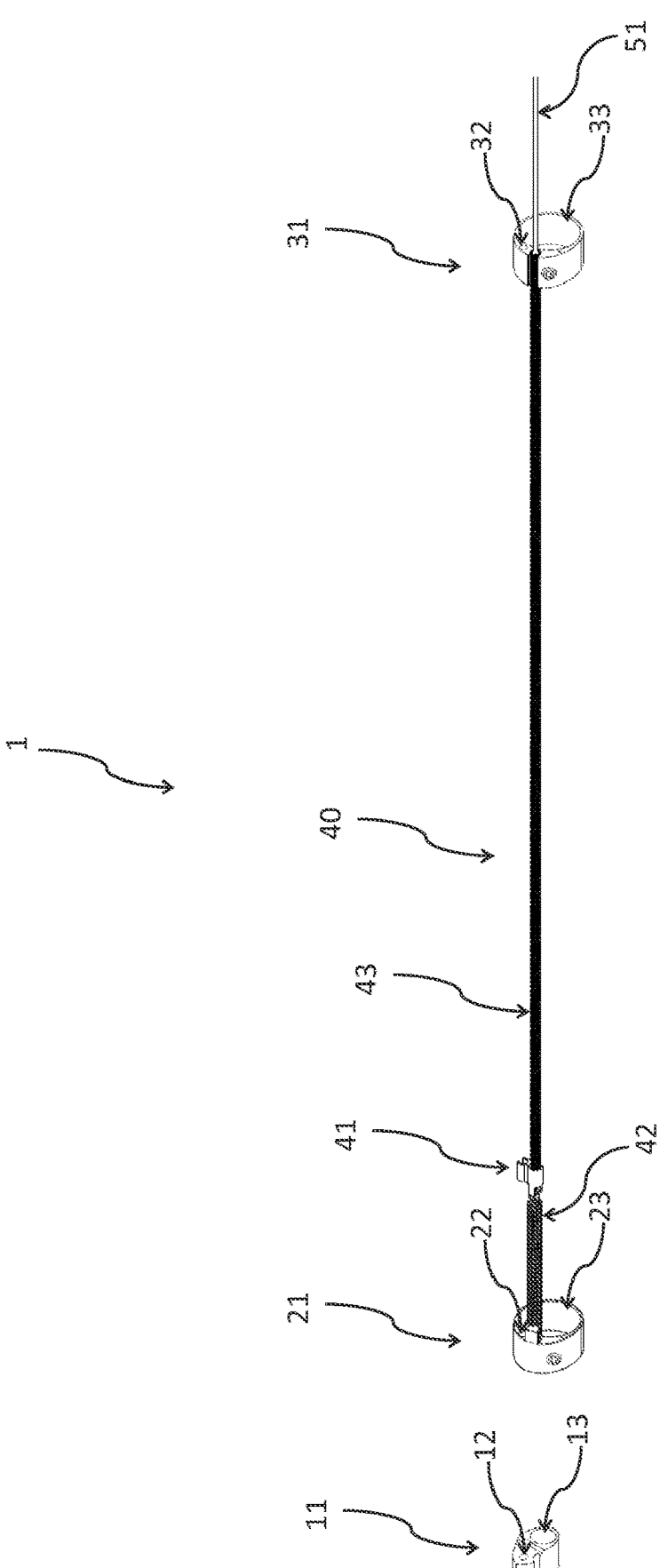
FIG. 1B is a side view of a device according to embodiments of the disclosure when not coupled to a laser fiber and surgical instrument.

Referring to FIGS. 1A and 1B, a device 1 for removably attaching a laser fiber 2 to a surgical instrument 3, according to embodiments of the disclosure, is shown. The surgical instrument 3 comprises a shaft 4 that extends in a first direction z between a tip 5 and a base (100). In the example implementation shown in FIG. 1, the surgical instrument 3 is a monopolar spatula 7. However, the disclosure is not limited to devices for attaching a laser fiber to a monopolar spatula; the surgical instrument may be, for example, monopolar hook, bipolar scissors, bipolar forceps, curved bipolar dissectors, vessel sealer, clip applier, needle driver.

The monopolar spatula 7 has at the tip end a cauterizing element 8 to which electrical current can be provided. The cauterizing element 8 is held within a mount 9. The monopolar spatula 7 comprises tip actuation means 10 for causing rotation of the mount 9, and therefore also the cauterizing element 8, about an axis y perpendicular to the first direction z.

Referring to FIGS. 1B, 2, 3A, and 3B, the device 1 comprises a first coupling element 11 for coupling the fiber 2 to the instrument 3. The first coupling element 11 comprises a first aperture 12 for slidably coupling (i.e., coupling in a slidable manner) to the fiber 2, for example, the aperture may be in the form of a cylindrical aperture that blocks 4 independent degrees of freedom (DOFs) of the fiber, leaving translation in the first direction and rotation about an axis z' parallel to the first direction z free. In some embodiments, the aperture may be in the form of a joint that blocks 5 DOFs, leaving only translation in the first direction free. For example, the aperture may have an elliptical shape for fitting a fiber with an elliptical cross-section, which would be blocked from rotating about the axis z'. The first coupling element 11 comprises a second aperture 13 for fixedly coupling to the instrument 3. The second aperture 13 is configured to receive and then couple to the instrument 3 such that the instrument 3 can slide within the second aperture 13, then is fixed after coupling. For example, a set screw (not shown) may be used to fix the instrument 3 to the first coupling element 11.

In the example embodiment shown in FIG. 1A, the first coupling element 11 is configured to fixedly couple to the monopolar spatula 7 at the mount 9. Thus, when tip actuation means 10 is actuated so as to rotate the mount 9, the first coupling element 11 and therefore also the fiber 2 are rotated as well. In the example embodiment shown in FIG. 1A, the actuation means 10 comprises two different pulleys, providing two orthogonal rotational degrees of freedom that can be used to position the location of the fiber 2. In some embodiments, the actuation means comprises a single pulley providing a single rotational degree of freedom.

Figure 2:
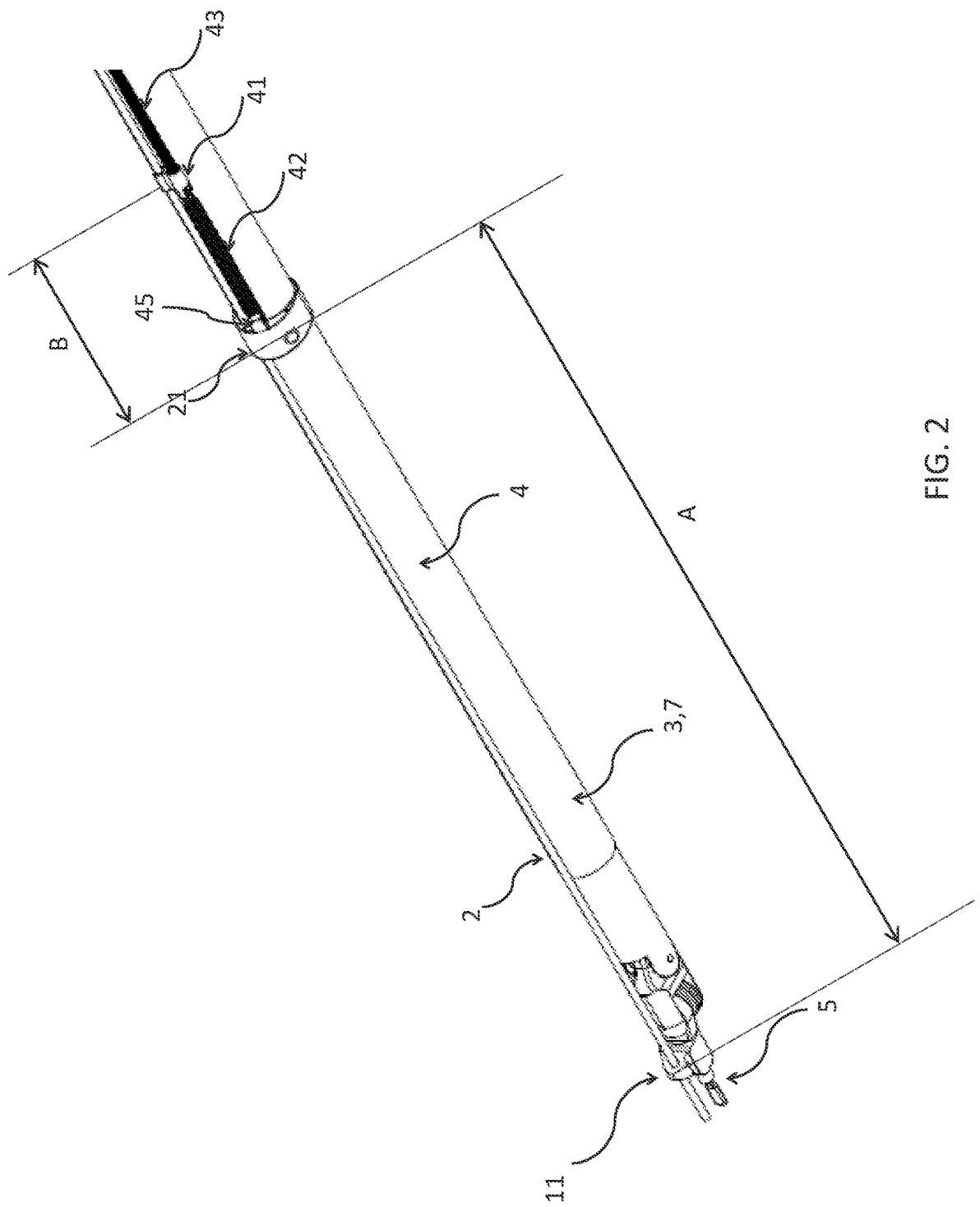
FIG. 2 is a perspective view of first and second coupling elements of a device according to embodiments of the disclosure when coupled to a laser fiber and a surgical instrument.
Figure 3A:
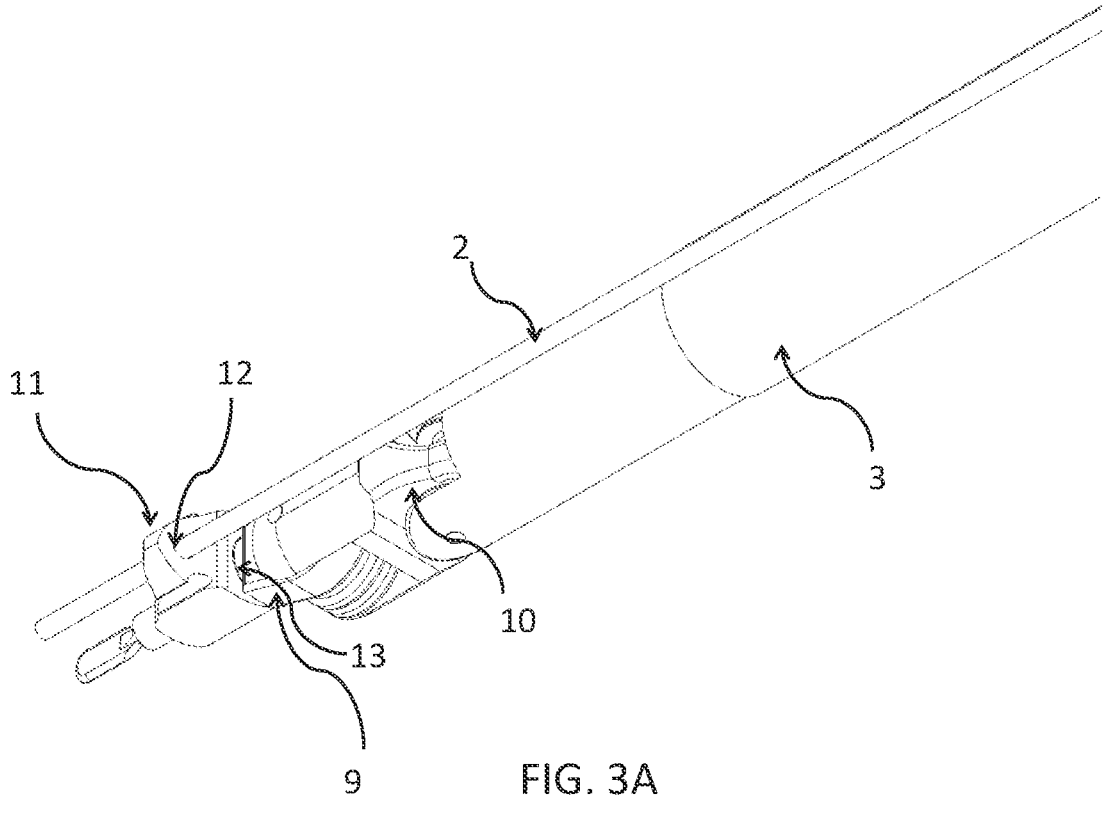
FIG. 3A is a perspective view of a first coupling element of a device according to embodiments of the disclosure when coupled to a laser fiber and a surgical instrument.
Figure 3B:
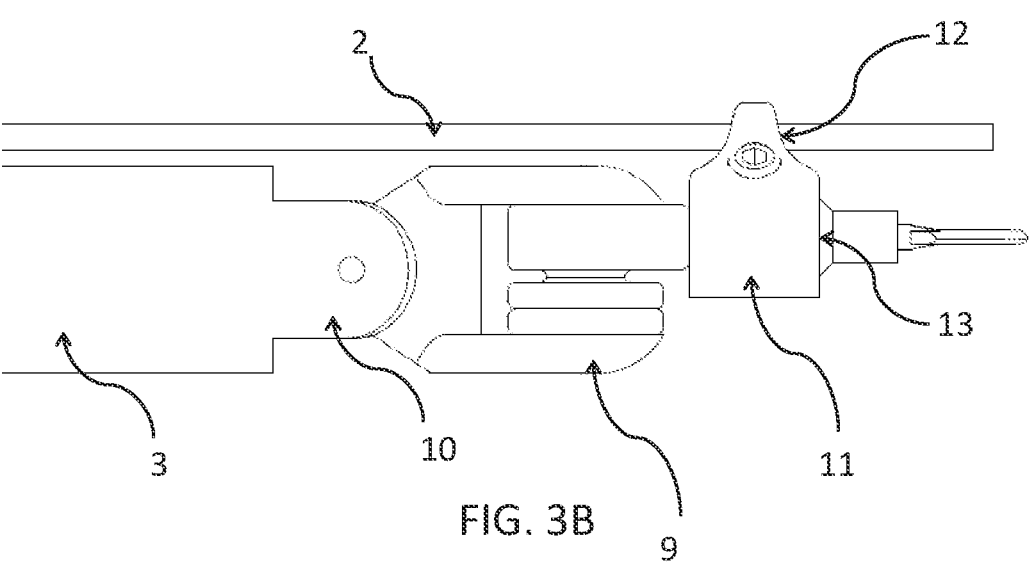
FIG. 3B is a side view of a first coupling element of a device according to embodiments of the disclosure when coupled to a laser fiber and a surgical instrument.
Figure 3C:
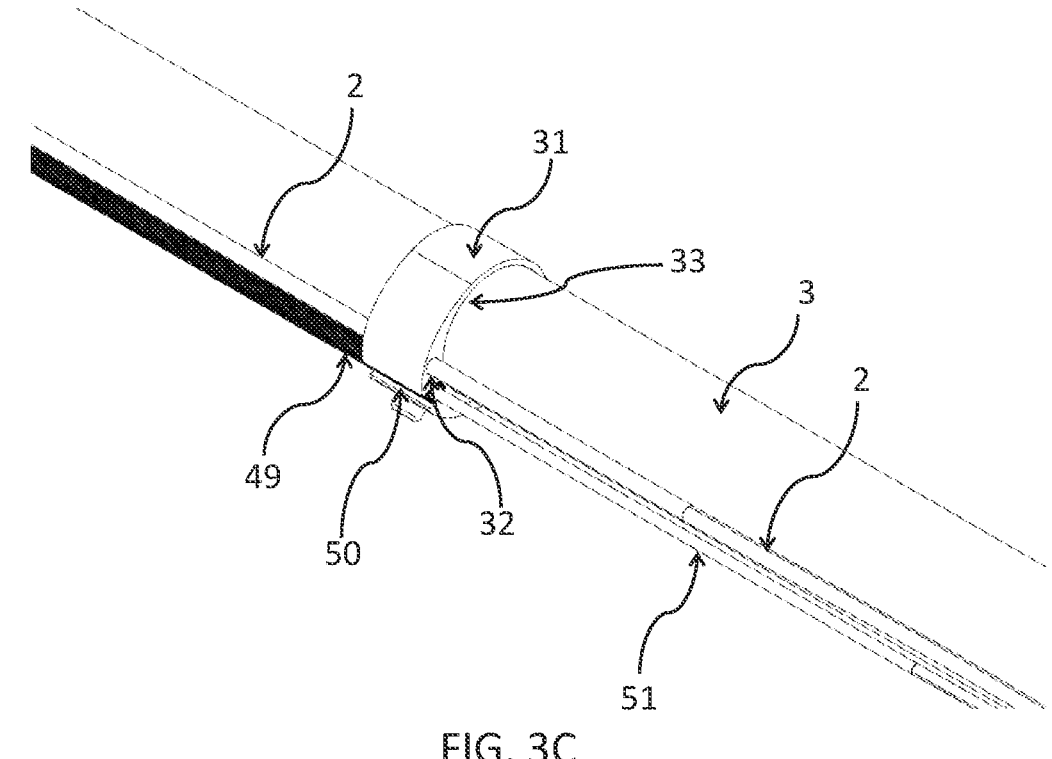
FIG. 3C is a perspective view of a third coupling element of a device according to embodiments of the disclosure when coupled to a laser fiber and a surgical instrument.
Figure 3D:
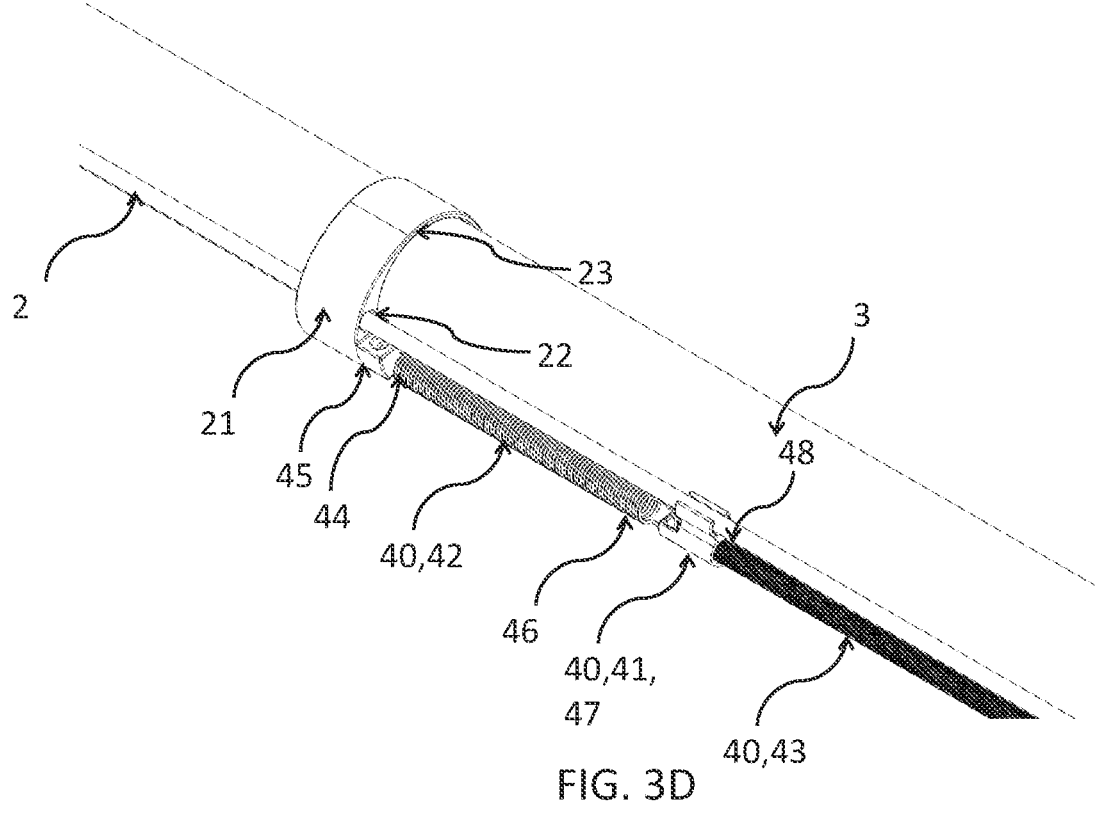
FIG. 3D is a perspective view of a second coupling element of a device according to embodiments of the disclosure when coupled to a laser fiber and a surgical instrument.
Figure 3E:
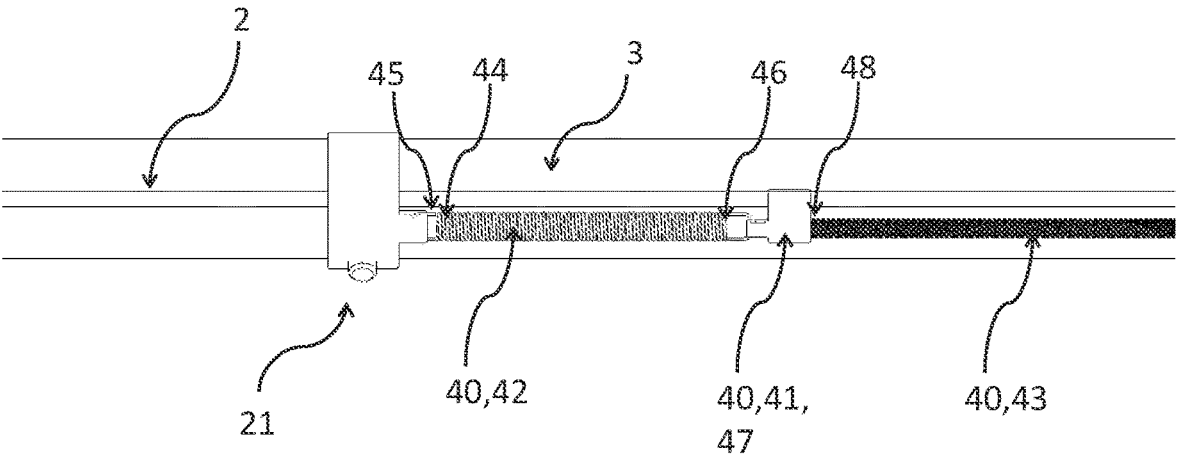
FIG. 3E is a side view of a second coupling element of a device according to embodiments of the disclosure when coupled to a laser fiber and a surgical instrument.

Referring to FIGS. 1B, 2 and 3D, the device 1 comprises a second coupling element 21 for coupling the fiber 2 to the instrument 3. The second coupling element 21 comprises a first aperture 22 for slidably coupling (i.e., coupling in a slidable manner) to the fiber 2, for example, the aperture may be in the form of a cylindrical joint that blocks 4 degrees of freedom (DOFs) leaving translation in the first direction and rotation about an axis z' parallel to the first direction z free. In some embodiments, the aperture may be in the form of a joint that blocks 5 DOFS, leaving only translation in the first direction free. For example, the aperture may have an elliptical shape for fitting a fiber with an elliptical cross-section that would be blocked from rotating about the axis z'. The second coupling element 21 comprises a second aperture 23 for fixedly coupling to the instrument 3. The second aperture 23 is configured to receive and couple to the instrument 3 such that the instrument 3 does not slide within the second aperture 23. For example, a set screw (not shown) may be used to fix the second coupling element 21 to the instrument 3. When the device 1 is attached to the instrument 3, the second coupling element 21 is spaced apart from the first coupling element 11 in a direction parallel to the first direction such that the first coupling element 11 is between the tip 5 and the second coupling element 21. The separation A between the first coupling element 11 and the second coupling element 21 is greater than or equal to the product of the minimal bending radius and the maximum expected bending angle of the fiber 2.

The minimal bending radius is the smallest radius the fiber can be subjected to by bending without damage or reducing the fiber power transmission of the laser to the point of ineffective cutting, e.g., to power transmissions that are lower than 10% of the nominal laser power. The minimal bending radius is typically expressed in terms of the fiber diameter and depends on the type of laser and fiber used. The minimal bending radius may be, for example, between 10 times and 50 times the fiber diameter, for example, 10 times the fiber diameter, 20 times the fiber diameter, 30 times the fiber diameter, 40 times the fiber diameter, 50 times the diameter. The fiber used in the example embodiment shown in FIG. 1 has a recommended minimum bend radius of 40 mm for a diameter of 1.04 mm. The maximum expected bending angle is 70° in pitch, 90° in yaw.

The different motion degrees of freedom are expressed with respect to an orthonormal coordinate frame that is attached to the instrument shaft 4 in such a way that the frame's z-axis is aligned along the longitudinal axis of the shaft and that the x-axis is parallel to the proximal (first) axis of the wristed joint/actuation means 10. The y-axis of the coordinate frame is aligned such as to form a right-handed coordinate frame. With respect to this reference coordinate frame, the roll axis of the instrument shaft 4 corresponds to a rotation about the z-axis of the coordinate frame. The instrument's yaw angle corresponds to a rotation about an axis parallel to the y-axis of the coordinate frame and the instrument's pitch angle corresponds to a rotation about an axis parallel to the x-axis of this coordinate frame. The wristed yaw and wristed pitch angles correspond to rotations about axis that are respectively parallel to the y- and x-axis of the coordinate frame when considering the wrist extended in its neutral position (i.e., fully stretched). It is understood that other conventions of angles may be employed to describe the pose (orientation and position) of respective components of the instrument such as Euler angle notations, equivalent angle-axis aligned, unit quaternions, or other definitions of roll-pitch-yaw axes along differently positioned coordinate frames.

Referring to FIGS. 1A, 1B, 3D, and 3E, in some embodiments the device 1 comprises a third coupling element 31 for coupling the fiber 2 to the instrument 3. The third coupling element 31 comprises a first aperture 32 for slidably coupling (i.e., coupling in a slidable manner) to the fiber 2, for example, the aperture may be in the form of a cylindrical joint, which blocks 4 degrees of freedom, (DOFs) leaving translation in the first direction and rotation about an axis z' parallel to the first direction z free. In some embodiments, the aperture may be in the form of a joint, which blocks 5 DOFS, leaving only translation in the first direction free. For example, the aperture may have an elliptical shape for fitting a fiber with an elliptical cross-section, which would be blocked from rotating about the axis z'. The third coupling element 31 comprises a third aperture 33 for fixedly coupling to the instrument 3. The first aperture 32 is configured to receive the fiber 2 such that the fiber 2 can slide within the first aperture 32 in a direction parallel to the first direction z. The second aperture 33 is configured to receive the instrument 3 such that the instrument 3 does not slide within the second aperture 33. For example, a set screw (not shown) may be used to fix the second coupling element 31 to the instrument 3. The second aperture 33 preferably receives the shaft 4 of the instrument 3 in use. When the device 1 is attached to the instrument 2, the second coupling element 21 is located between the first coupling element 11 and the third coupling element 31 and preferably in a direction parallel to the first direction z.

The device may be configured to couple to the instrument through the corresponding apertures of the first, second, and third coupling elements using fixing means other than a set screw, e.g., using glue, soldering, welding, tightening collars, removable snap-fit mechanisms, bi-stable flexure mechanisms. In another embodiment any of the coupling elements may be manufactured in an integrated fashion, forming a single part with the corresponding portion of the instrument 3.

Referring still to FIGS. 1A, 1B, 3D, and 3E, the device 1 comprises an actuation element 40 connected between the second coupling element 21 and the third coupling element 31. The actuation element 40 comprises a connector 41 that is configured to fixedly couple to the fiber 2. When actuated, the actuation element 40 causes the connector 41 to be translated along the first direction z. Thus, when the fiber 2 is fixedly coupled to the connector 41, the fiber 2 is also translated along the first direction when the actuation element 40 is actuated. In the example embodiment shown in FIG. 1, the actuation element 40 comprises a spring 42 and a pneumatic artificial muscle 43. The spring 42 and the pneumatic artificial muscle 43 serve together as bi-directional actuator. The spring 42 is attached at a first end 44 to the second coupling element 21 at a coupling point 45 on the second coupling element 21. The spring 42 is attached at a second end 46 to a rigid spring-muscle connector 47 (connector 41). The artificial muscle 43 is attached at a first end 48 to the rigid spring-muscle connector 47 (connector 41) and is attached at a second end 49 to a coupling point 50 on the third coupling element 31. A pneumatic air supply 51 capable of providing pressurized air to the artificial muscle 43 is connected to the artificial muscle 43 at coupling point 50 on the third coupling element 31.

The actuation element 40 allows the distance B between the second coupling element 21 and the connector 41 in a direction parallel to the first direction z to be varied as follows. In a neutral state, with no air supplied to the artificial muscle 43, the muscle 43 has a length $I_1$ and the spring 42 has a length $I_2$, which is equal to a slightly pre-tensioned length. The spacing between the second coupling element and the connector 41 is $B_1=I_2$. In a muscle contracted state, in which pressurized air is supplied to the muscle 43, the muscle 43 has a length $I_3$, which is less than $I_1$. As the first end 44 of the spring 42 is fixed to the second coupling element 21, which is, in turn, fixed to the instrument 3, and the second end 49 of the muscle 43 is fixed to the second coupling element 31, which is fixed to the instrument 3, contraction of the muscle 43 causes the connector 41 to slide along the instrument 3 toward the third coupling element 31. This causes the spring 42 to be elongated to a length $I_4$, which is more than 12. Thus in the contracted configuration the spacing between the second coupling element and the connector 47 is $B_2=I_4$. By controllably decreasing the pressurized air supply to the muscle 43, the separation B can be reduced again as the spring 42, being in a stretched state, produces a force on the spring-muscle connector 47 in the direction of the coupling element 21. Thus the separation B can be controlled by controlling the air pressure supplied to the muscle 43.

Different embodiments may have different arrangements of muscles and springs to create bi-directional motion. For example, in another embodiment the muscle may reduce in diameter and elongate upon applying higher pressures.

Although in the preceding example the actuation element 40 is described as being a spring-muscle system, other possibilities for the connector are included in the scope of the disclosure. For example, in some embodiments the actuation element 40 may comprise a push-pull cable guided through a Bowden system, where the push/pull cable replaces the muscle and is rigidly fixed (e.g., glued) to the connector 41. In some embodiments, the actuation element 40 may comprise a pulley system that would loop around the second coupling element 21. In some embodiments the actuation element 40 may comprise smart materials such as shape-memory alloys (SMA), electro-active polymers, ionic polymer or other types of actuators or linear actuators that change length when current or voltage is applied. In some embodiments, the actuation element 40 may comprise a cable and a motor. In some embodiments, the actuation element may comprise two antagonistic muscles; for example, in a two-coupling-element embodiment, the actuation element may comprise a first muscle connected to the first coupling element and the connector 41, and a second muscle connected to the connector 41 and the second coupling element, wherein the muscles are configured to operate in an antagonistic manner such that when one muscle expands, the other muscle contracts and vice versa. In a three coupling element embodiment, the first muscle would be connected to the second coupling element and the connector 41, and the second muscle would be connected to the connector 41 and the third coupling element. As the fiber is, in use, fixed to the connector 41 and capable of sliding in the apertures of the first, second and third coupling elements 11, 21 and 31 by changing the distance between the second coupling element 21 and the connector 41 through actuation of the actuation element 40, the fiber can be translated with respect to the surgical instrument in a direction parallel to the first direction z. This provides a third degree of freedom of actuation of the fiber.

The device may be linked to a control system for controlling the sliding of the fiber through the apertures via the pneumatic air supply. For example, one control strategy that may be used in embodiments of the disclosure is to provide a system comprising the device according to embodiments of the disclosure and a foot pedal (not shown) that is linked to an air supply unit and is programmed to switch between three different positions of the laser fiber tip relative to the monopolar spatula tip:

1. Fully retracted position: the laser fiber tip is retracted to a position behind the monopolar spatula tip, e.g., 8 mm behind, allowing the monopolar spatula to be used for cutting/cauterization and/or blunt dissection.
2. The intermediate position: the laser fiber tip is protracted to a position behind the monopolar spatula tip, which is closer to the tip than position 1, e.g., 2 mm behind, allowing to use the laser-fiber for cutting. As $CO_2$— laser fiber cutting properties are optimal when the distance between the laser fiber tip and the tissue is approximately 2 mm, gently touching the tissue during surgery with the spatula tip automatically indicates the optimal distance between laser tip and tissue. This configuration is preferable when operating with a straight monopolar spatula; bending the distal tip (in the pitch or yaw direction or combinations thereof) of the monopolar spatula during surgery can lead to changes in the relative distance between laser tip and spatula tip.
3. Fully extended position: the laser fiber tip is protracted to a position in front of the monopolar spatula tip, e.g., 5 mm in front, allowing to reach deeper with the laser fiber. It also allows use of the laser fiber during extreme pitch positions of the spatula tip.

Other control strategies may be implemented in embodiments of the disclosure. For example, any number of discrete positions can be implemented for the strategy described hereinbefore.

Embodiments of the disclosure provide systems for control of a device according to embodiments as described herein.

A system according to embodiments of the disclosure may comprise a device as described hereinbefore and a control module comprising control means for controlling the position of the connector relative to the second coupling element and optional imaging means and display means for viewing a current configuration of the device.

The imaging means may comprise a camera or video camera for transmitting an image of the device to a display means, allowing an operator of the device to have visual feedback on the position, orientation, and/or configuration of the device.

The control means may comprise one or more of a rotary dial, sliding pin, joystick, voice control, "forward" and "backward" buttons, sensing glove with one or more sensorized fingertips, in communication (for example, electrically connected with) the actuation element. The control means is interfaced with the actuation element such that the control means is capable of causing the actuation element to actuate, thus translating the connector. For example, in embodiments wherein the actuation element comprises an artificial muscle and a spring and the control means comprises a rotary dial, the rotary dial may be connected between a power supply and an input to a controller for the air supply for the artificial muscle. By rotating the rotary dial, the input power to the controller is varied and thus the extension/contraction of the muscle, and therefore the movement of the connector are varied.

If the surgical instrument is part of a surgical robot, control of the device may be provided by providing an additional button or control element on the main robot master control.

In some embodiments, the instrument 3 does not comprise tip actuation means 10 for actuating the tip and the fiber can only be actuated in the direction parallel to the first direction z.

The add-on nature of the device according to embodiments of the disclosure means that no definitive modifications or only minor modifications are needed to the robotic instruments. This is a particular advantage in robotic surgery applications as the robotic platform is typically shared between multiple surgical specialties; the disclosure allows the same robotic instruments to be used for various different specialties. Additionally, the "add-on" principle of the disclosure avoids interference with robotic instrument cleaning and sterilization. The device is suitable for ethylene oxide sterilization or can be single-use.

Figure 4:
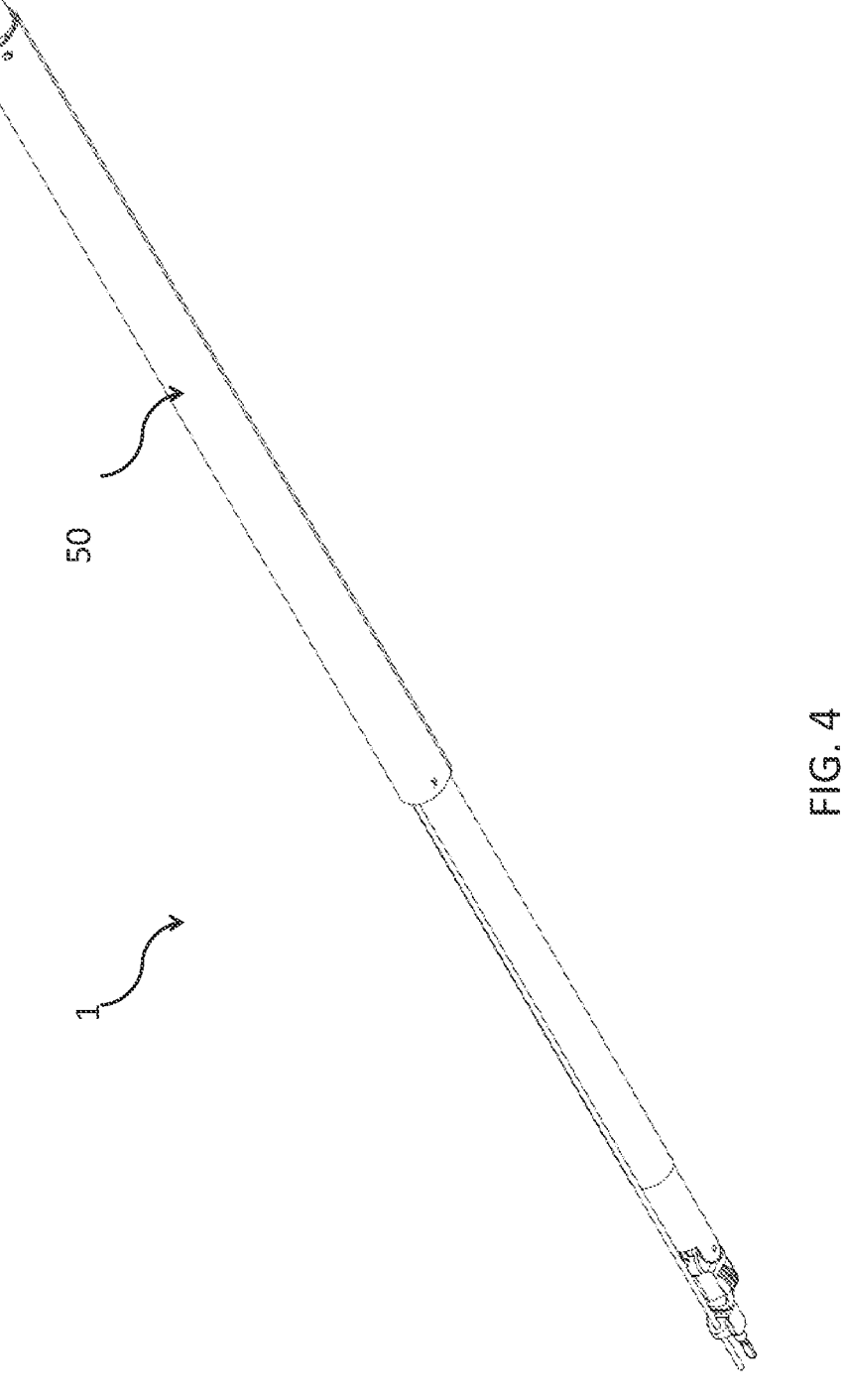
FIG. 4 is a perspective view of a device according to embodiments of the disclosure when coupled to a laser fiber and a surgical instrument, the device comprising a rigid sheath covering the second and third coupling elements.

Referring to FIG. 4, the device 1 may comprise an outer rigid sheath 50 that extends over the second and third coupling elements 21, 31 and the connector 40. The sheath 50 allows the connector 40 and coupling elements 21, 31 to be protected from other surgical instruments or the patient anatomy. The sheath is preferably attached to the second and third coupling elements 21, 31 using set screws, allowing the device 1 to be slid on and off the instrument easily.

Figure 5:
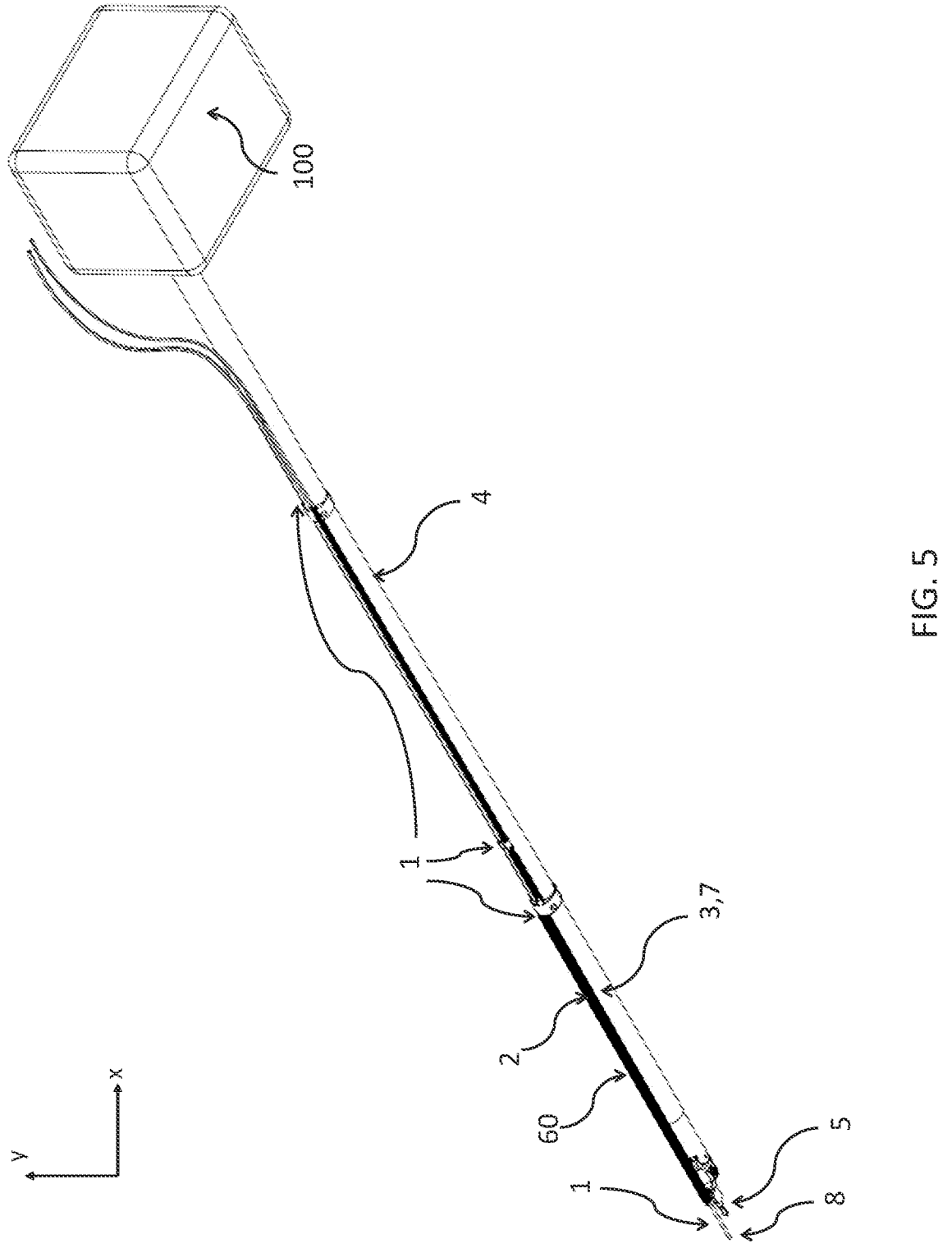
FIG. 5 is a perspective view of a device according to embodiments of the disclosure when coupled to a laser fiber and a surgical instrument, the device comprising a sheath covering the fiber between the first and second coupling elements.

Referring to FIG. 5, the device 1 may comprise an outer bendable sheath 60 that extends between the first and the second coupling elements 11 and 21. The sheath 60 preferably has a low bending stiffness (below the bending stiffness of the laser) and a high axial stiffness (comparable or higher than the axial stiffness of the laser fiber) and an inner surface with low friction coefficient (e.g., below 0.05) providing a support for the bendable laser fiber, allowing the fiber to slide with minimal friction through the sheath, and action, which is to a Bowden cable. The sheath provides a more precise linear displacement of the laser fiber. The sheath 60 may be positioned between the first and second coupling elements or may be rigidly connected to one or more of the coupling elements.

Figure 6:
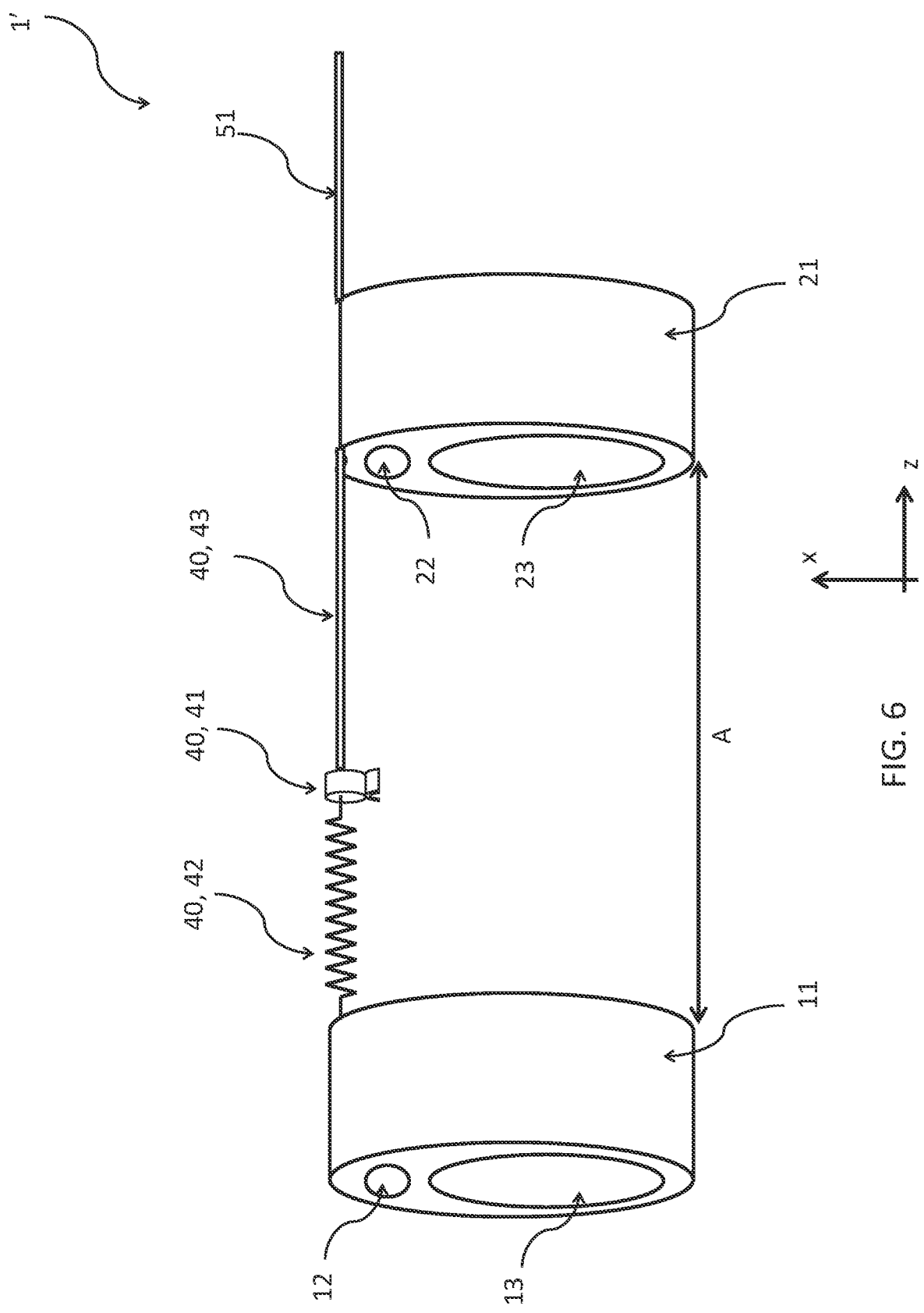
FIG. 6 is a side view of a device according to embodiments of the disclosure that does not comprise the third coupling element.

Referring to FIG. 6, a modified device 1' according to embodiments of the disclosure comprises only the first and the second coupling elements 11, 21, that is, the third coupling element 31 is not included. The actuation element 40 is then connected between the first and the second coupling elements.

In some embodiments the device may contain a method to estimate the linear motion of the actuator, e.g., based on current supplied to an SMA, pressure supplied to a pneumatic muscle or similar.

In some embodiments the device may contain a sensor to measure the linear motion of the actuator. For example, the artificial muscle may have a capacitive sensing capability following the principles as disclosed in J. Legrand, B. Loenders, A. Vos, L. Schoevaerdts, and E. Vander Poorten (2019), Integrated Capacitance Sensing for Miniature Artificial Muscle Actuators, Ieee Sensors Journal, or any other compact means of measuring the motion of the actuator. For example, by adding an optical fiber and estimating the distance based on variations in light intensity, a principle that was used to estimate forces in the work from J. Peirs, J. Clijnen, D. Reynaerts, H. Van Brussel, P. Herijgers, B. Corteville, and S. Boone (2004), A micro-optical force sensor for force feedback during minimally invasive robotic surgery, *Sensors and Actuators A,* 115 (2), 447-455.

In some embodiments the displacement of the laser fiber may be measured, for example, the device may comprise an optical sensor that is placed outside the body, directed at a side of the laser fiber, the artificial muscle or the connector, and a controller for the optical sensor configured to receive measurements from the optical sensor and to determine a displacement of the fiber based on the received measurements based on optical flow. The device may comprise a pair of rotating pulleys between which the fiber can be arranged and a controller for receiving a measurement of rotation angle of the pulleys from, e.g., an encoder or potentiometer coupled to one or both of the pulleys and configured to determine a displacement of the laser fiber based on the received measurements.

In some embodiments the estimated or measured motion of the actuator or the laser fiber may be used to improve the safety of the solution such as to generate a warning signal when slip, uncontrolled motion (e.g., due to failure of the actuator), overshoot or displacement stalls (e.g., due to failure of the actuator or large amount of debris). In some embodiments this motion or resistance of motion may be used to estimate possible contact between the fiber and the anatomy.

In some embodiments the estimated or measured motion may be used in a feed-forward, in a feedback or any other control approach to improve the positioning accuracy of the fiber, to avoid contact or establish contact between the fiber and the anatomy.

In some embodiments redundant sensing approaches may be used to ensure the sanity of the system and to signal warnings in case inconsistencies are detected. In some embodiments safety measures may be installed depending on inconsistencies between multiple sensor readings or between sensor readings and models of the system (and its actuator).

It is to be understood that although preferred embodiments, specific constructions and configurations, as well as materials, have been discussed herein for devices according to the present embodiment, various changes or modifications in form and detail may be made without departing from the scope and technical teachings of this description. For example, any formulas given above are merely representative of procedures that may be used. Functionality may be added or deleted from the block diagrams and operations may be interchanged among functional blocks. Steps may be added or deleted to methods described within the scope of the present embodiments.

What is claimed is:

1. A device for removably coupling a laser fiber to a shaft of a surgical instrument, the shaft extending in a first direction, the device comprising:

at least a first and a second coupling element for coupling the fiber to the instrument, each of the coupling elements comprising a respective first aperture for slidably coupling to a laser fiber and a respective second aperture for fixedly coupling to the instrument;

the first and second coupling elements being spaced apart in a second direction parallel to the first direction, the first element being positioned such that when coupled to the instrument, the first element is located between a first end of the shaft and the second element, the first and second element being spaced apart in the second direction by a separation that is greater than or equal to the product of the minimal bending radius and the maximum expected bending angle of the fiber; and the device further comprising an actuation element connected between two coupling elements, the actuation element comprising a connector for fixedly coupling to the fiber, wherein the actuation element is configured to translate the connector along the second direction when actuated.

2. The device of claim 1, wherein the actuation element comprises at least one artificial muscle.

3. The device of claim 2, wherein the actuation element comprises a spring.

4. The device of claim 3, wherein the connector connects the spring and the artificial muscle.

5. The device of claim 1, wherein the actuation element comprises a cable and the device comprises a motor for actuating the cable.

6. The device of claim 1, wherein the maximum expected bending angle is between 10 and 90 degrees.

7. The device of claim 2, wherein the maximum expected bending angle is between 10 and 90 degrees.

8. The device of claim 3, wherein the maximum expected bending angle is between 10 and 90 degrees.

9. The device of claim 4, wherein the maximum expected bending angle is between 10 and 90 degrees.

10. The device of claim 5, wherein the maximum expected bending angle is between 10 and 90 degrees.

11. The device of claim 1, further comprising:

a third coupling element, wherein the second coupling element is located between the first and the third coupling elements in the second direction, wherein the actuation element is connected between the second and the third coupling element.

12. The device of claim 2, further comprising:

a third coupling element, wherein the second coupling element is located between the first and the third coupling elements in the second direction, wherein the actuation element is connected between the second and the third coupling element.

13. The device of claim 3, further comprising:

a third coupling element, wherein the second coupling element is located between the first and the third coupling elements in the second direction, wherein the actuation element is connected between the second and the third coupling element.

14. The device of claim 4, further comprising:

a third coupling element, wherein the second coupling element is located between the first and the third coupling elements in the second direction, wherein the actuation element is connected between the second and the third coupling element.

15. The device of claim 5, further comprising:

a third coupling element, wherein the second coupling element is located between the first and the third coupling elements in the second direction, wherein the actuation element is connected between the second and the third coupling element.

16. The device of claim 11, further comprising:

a rigid sheath that extends over the second and third elements and the actuation element.

17. The device of claim 1, further comprising a bendable sheath that extends between the first and second elements for enclosing a portion of the laser fiber between the first and second elements.

18. The device of claim 2, further comprising a bendable sheath that extends between the first and second elements for enclosing a portion of the laser fiber between the first and second elements.

19. The device of claim 11, further comprising a bendable sheath that extends between the first and second elements for enclosing a portion of the laser fiber between the first and second elements.

20. A system comprising:

the device of claim 1, and a control module comprising:

control means for controlling a position of the connector relative to the second coupling element and means for estimating the motion of the actuator, for measuring the configuration of the device or for measuring displacement of the laser fiber.

* * * * *